(12) United States Patent
Gair, Jr.

(10) Patent No.: US 12,161,572 B2
(45) Date of Patent: Dec. 10, 2024

(54) MODULAR PROSTHESIS SYSTEM

(71) Applicant: Scinetics, Inc., Abingdon, MD (US)

(72) Inventor: Jeffrey L. Gair, Jr., Abingdon, MD (US)

(73) Assignee: SCINETICS, INC., Abingdon, MD (US)

(*) Notice: Subject to any disclaimer, the term of this patent is extended or adjusted under 35 U.S.C. 154(b) by 513 days.

(21) Appl. No.: 17/308,737

(22) Filed: May 5, 2021

(65) Prior Publication Data
US 2021/0353441 A1    Nov. 18, 2021

Related U.S. Application Data

(60) Provisional application No. 63/023,375, filed on May 12, 2020.

(51) Int. Cl.
*A61F 2/80*   (2006.01)
*A61F 2/50*   (2006.01)
(Continued)

(52) U.S. Cl.
CPC ............ *A61F 2/80* (2013.01); *A61F 2/76* (2013.01); *A61F 2002/503* (2013.01); *A61F 2002/5083* (2013.01); *A61F 2002/7868* (2013.01)

(58) Field of Classification Search
CPC ........ A61F 2/80; A61F 2/76; A61F 2002/503; A61F 2002/5083; A61F 2002/7868;
(Continued)

(56) References Cited

U.S. PATENT DOCUMENTS 2,229,728 A * 1/1941 Eddels ............... A61F 2/80
                                                      623/36
3,550,311 A * 12/1970 Fouquart ........... A63H 33/065
                                                     446/120
(Continued)

FOREIGN PATENT DOCUMENTS

EP    3639794 A1 *   4/2020
GB    127451 A        6/1919
(Continued)

OTHER PUBLICATIONS

Martin Bionics Innovations LLC, Socket-less Socket, Website, Oklahoma City, Oklahoma, https://martinbionics.com/above-elbow-socket-less-socket/.
(Continued)

*Primary Examiner* — Jerrah Edwards
*Assistant Examiner* — Maximilian Tobias Spencer
(74) *Attorney, Agent, or Firm* — Husch Blackwell LLP

(57) ABSTRACT

The disclosure describes an adjustable modular prosthesis system comprising of repeating and interconnecting modular linkages. The modular linkages can be configured in a number of ways to form a network of modular linkages that comprise an adjustable custom socket around the limb of a user. The disclosed system further comprises a tensioning system that allows a user to control the socket's fit around their limb. The disclosed prosthesis system has a very low unique part count, may be mass-produced at low cost, and provides easy-to-use means of adjusting the shape and size of the socket to correspond with changes in a user's limb.

18 Claims, 12 Drawing Sheets

(51) Int. Cl.
*A61F 2/76* (2006.01)
*A61F 2/78* (2006.01)

(58) Field of Classification Search
CPC ...... A61F 2/60; A61F 2/601; A61F 2002/607; A61F 2002/608; A61F 2/54; A61F 2002/543; A61F 2002/546
See application file for complete search history.

(56) References Cited

U.S. PATENT DOCUMENTS

| | | | |
|---|---|---|---|
| 6,500,210 B1* | 12/2002 | Sabolich | A61F 2/583 623/24 |
| 8,795,385 B2 | 8/2014 | Bache | |
| 9,050,202 B2 | 6/2015 | Bache et al. | |
| 9,248,033 B2 | 2/2016 | Bache | |
| 10,092,424 B2 | 10/2018 | Bache | |
| 10,426,640 B2 | 10/2019 | Bache | |
| 10,543,112 B2 | 1/2020 | Bache et al. | |
| 2009/0076625 A1 | 3/2009 | Groves | |
| 2014/0135946 A1* | 5/2014 | Hurley | A61F 2/5044 623/33 |
| 2014/0277584 A1 | 9/2014 | Hurley et al. | |
| 2014/0288670 A1 | 9/2014 | Phillips | |
| 2018/0221179 A1 | 8/2018 | Bache et al. | |
| 2019/0000659 A1 | 1/2019 | Lecomte et al. | |
| 2019/0069641 A1* | 3/2019 | Soderberg | A43C 11/165 |
| 2019/0183663 A1 | 6/2019 | Will et al. | |
| 2019/0380848 A1* | 12/2019 | Hurley | A61F 2/66 |
| 2020/0022826 A1 | 1/2020 | Bache | |
| 2020/0170811 A1* | 6/2020 | Smith | A61F 2/76 |

FOREIGN PATENT DOCUMENTS

| | | |
|---|---|---|
| WO | WO2020078864 | 4/2020 |
| WO | WO-2020078864 A1 * | 4/2020 |
| WO | WO2021231633 A1 | 11/2021 |

OTHER PUBLICATIONS

Harry Kim (Authorized Officer), Written Opinion of the International Searching Authority re PCT/US2021/032071, Patent Cooperation Treaty, Aug. 7, 2021, Alexandria, VA.

* cited by examiner

100

200

1300

1400

MODULAR PROSTHESIS SYSTEM

FIELD OF THE INVENTION

The disclosure of the present patent invention relates to prosthetics and prosthesis systems.

BACKGROUND

Prosthesis systems (or prosthetic devices) connect a residual limb of a user to a prosthetic limb. A typical prosthesis system consists of a custom fitted socket that enwraps the residual limb, the prosthesis or artificial limb, cuffs and belts that attach it to the body, and prosthetic liners that cushion the area which contacts the skin. Prosthesis systems and specifically the sockets are not mass-produced and sold in stores. Instead, like dentures or eyeglasses, prosthetic devices are prescribed by a clinical practitioner after consultation with the patient, a prosthetist, and a physical therapist. Sockets must be custom made to securely fit the residual limb of a patient. Sockets generally must be fit by a clinical prosthetist. A prosthetist requires extensive training to learn how to mold, align, and fit a socket to an individual's limb.

Current prosthetic sockets require a complex and labor-intensive manufacturing process. A prosthetist must take several measurements of the residual limb to create a plaster cast of the residual limb. From there, a thermoplastic sheet is heated and vacuum-formed around the plaster mold to form a test socket. The prosthetist works with the patient to ensure the test socket fits, makes required modifications, and then creates a permanent socket. Optimal socket fit between the residual limb and socket is critical because it impacts the functionality and usability of the prosthesis system. If the socket is too loose, it can reduce areas of contact and create pockets between the residual limb and socket or liner. Pockets can accumulate sweat which damages the skin and results in rashes. If the socket is too tight, it increases contact pressure on the skin causing it to break down over time.

Current prosthesis systems are unable to adjust to changes in an individual's limb size. If the limb does not fit within the socket properly, it can render the prosthetic device less effective, ineffective, or even hazardous if it becomes unstable, for example, while the user is driving or walking. Consequently, patients have to see a prosthetist to remold, align, and fit a new socket which comes at a significant cost.

Prosthetic limbs require skilled operation that a patient must learn over time through extensive physical therapy. One issue patients face is the inability to feel sensation in the prostheses. Another issue is that patients experience phantom limb syndrome where the patient feels as if the amputated limb is still there. Consequently, performing even menial tasks requires active learning where the skill or task is explicitly practiced through a training regimen. Prosthesis embodiment refers to the ability of a user to operationalize a prosthesis as if it belonged to the body. Studies reveal that prosthesis embodiment is more likely to occur when the user engages in sensory learning. Sensory learning in this context refers to the application of sensory feedback on a patient's residual limb. Sensory feedback has been found to increase a user's willingness to use a prosthesis and leads to more active use.

Recent advances in prosthetic systems incorporate biofeedback that allows the user to "feel" through the prosthesis system. Specifically, sensors implanted on a user's residual limb can be used to provide physiologically appropriate sensory information to stimulate a patient's median and ulnar nerves enabling them to modulate the prosthesis without visual or auditory clues. Generally, these prosthesis systems either integrate sensors on the socket wall, insert sensors inside the socket, or embed sensors into the socket wall. Inserting sensors inside the socket requires extra thin, yet durable technology which restricts the number of options. Consequently, these systems tend to have poor accuracy and sensitivity. Integrating sensor systems on and into the socket require extensive work by a skilled prosthetist that is expensive and time consuming. Finally, prosthetic liners with sensor systems must be custom made to a user's requirements to avoid discomfort which requires a labor-intensive and expensive process.

Some prosthesis systems utilize microprocessors to interpret and analyze signals from angle and moment sensors. The microprocessors use these signals to determine the type of motion the patient is engaged in and modulates joints in the prosthesis accordingly, by varying the resistance to regulate the extension and compression of the prosthesis.

BRIEF DESCRIPTION OF THE FIGURES

The various advantages of the embodiments will become apparent to one skilled in the art by reading the following specification and referencing the following figures, in which.

DETAILED DESCRIPTION OF PREFERRED EMBODIMENTS

The following disclosure provides various embodiments of the disclosed invention to enable a person skilled in the art to make and use the invention exemplified in the embodiments. However, these embodiments are merely examples to simplify the disclosure and are not intended to be limiting.

Figure 1:
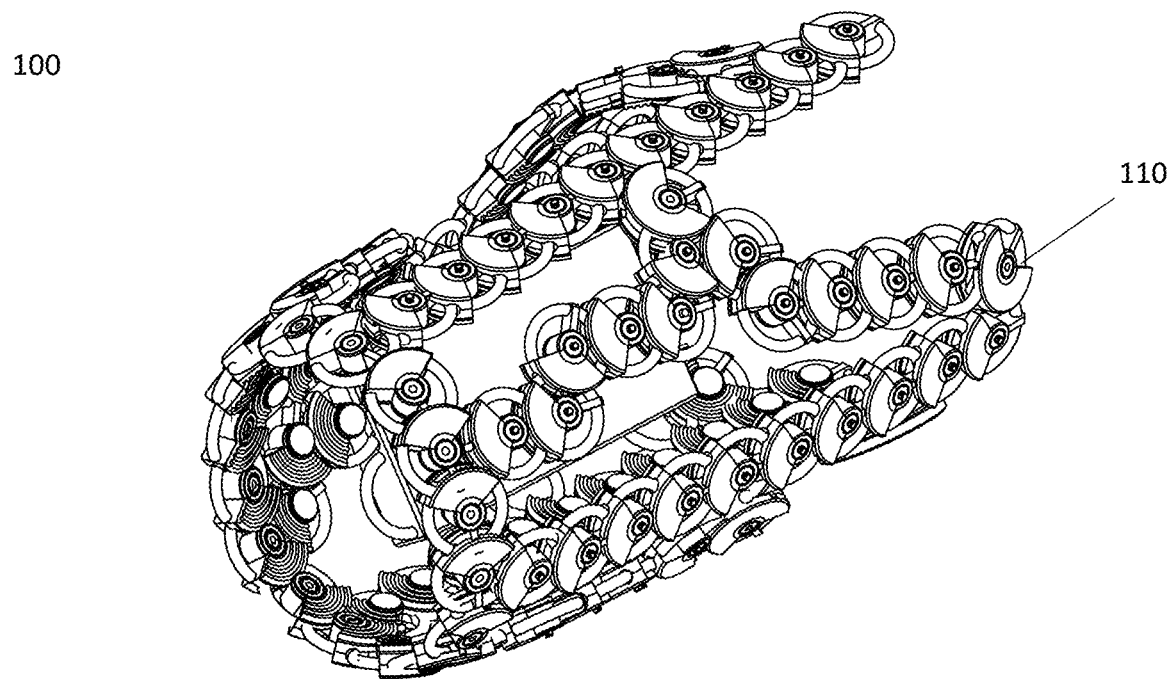
FIG. 1 is an embodiment of the prosthesis system comprising a network of repeating and interconnecting major and minor modular linkages to form a socket.
Figure 2:
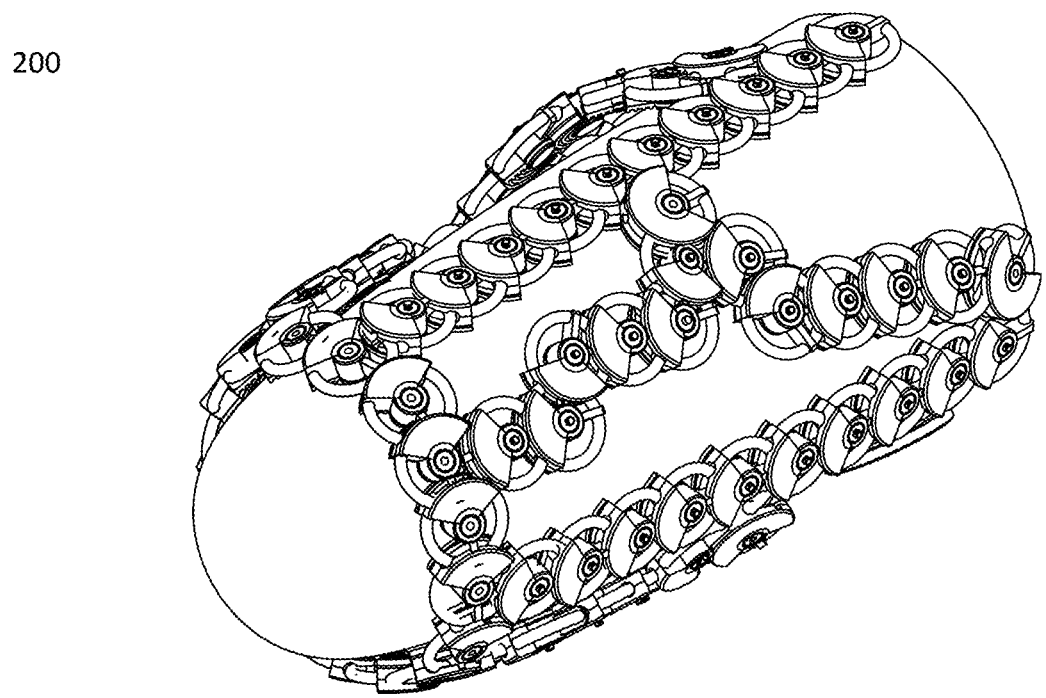
FIG. 2 is an embodiment of the prosthesis system comprising a network of repeating and interconnecting major and minor modular linkages to form a socket around a user's residual limb.

The disclosed invention is an adjustable prosthesis system 100. FIG. 1 shows an embodiment of the prosthesis system comprising repeating and interconnecting modular linkages 110. The modular linkages may be configured to form a socket that wraps around the limb of a user 200. This embodiment further comprises a mechanical coupling element 310/1710 which joins the socket to a prosthesis (prosthetic limb) by attaching to the prosthesis on one side 1720 and to a plurality of modular linkages on the other 1730. The prosthesis system comprises one or more tensioning elements 510 which may secure the plurality of modular linkages to the user's limb. One or more tensioners 520 are attached to the tensioning elements to allow the user to adjust the system's tension without clinical assistance.

Modular Linkages

Figure 6:
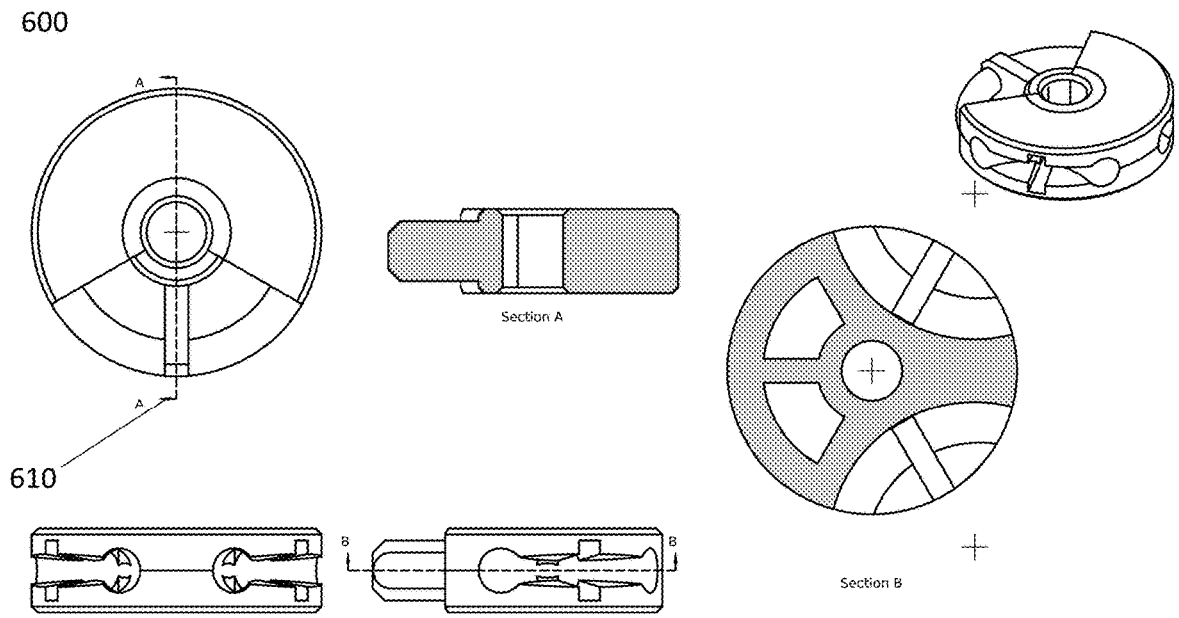
FIG. 6 shows cross-sectional views of an embodiment of a major modular linkage from top and side views.
Figure 7:
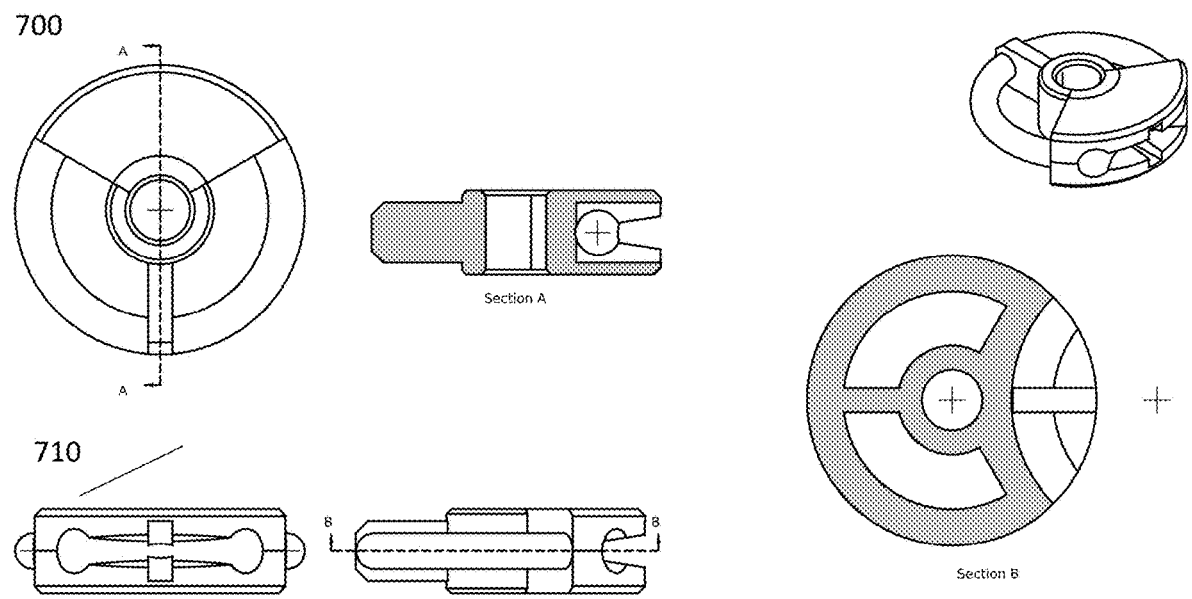
FIG. 7 shows cross-sectional views of an embodiment of a minor modular linkage from top and side views.
Figure 8:
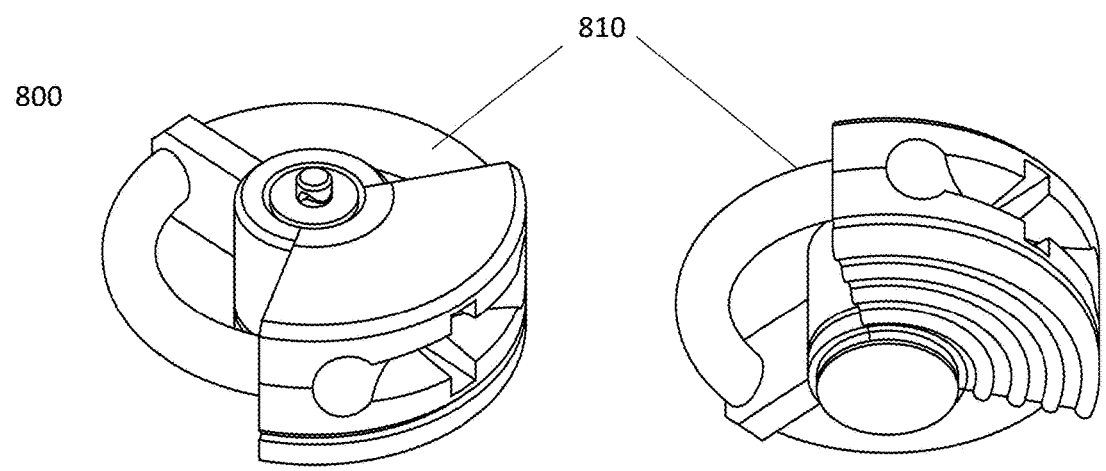
FIG. 8 shows isometric views of an embodiment of a minor modular linkage.
Figure 9:
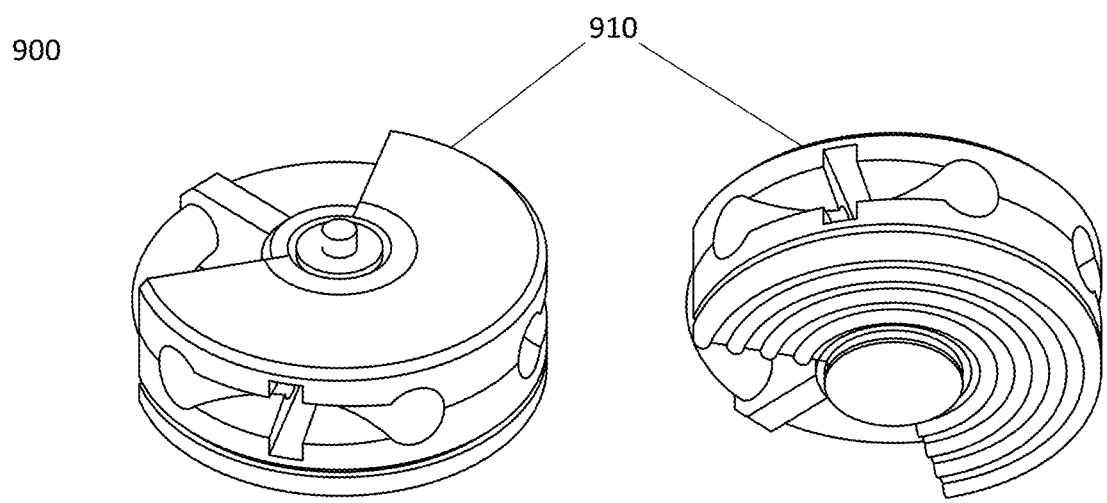
FIG. 9 shows isometric views of an embodiment of a major modular linkage.
Figure 10:
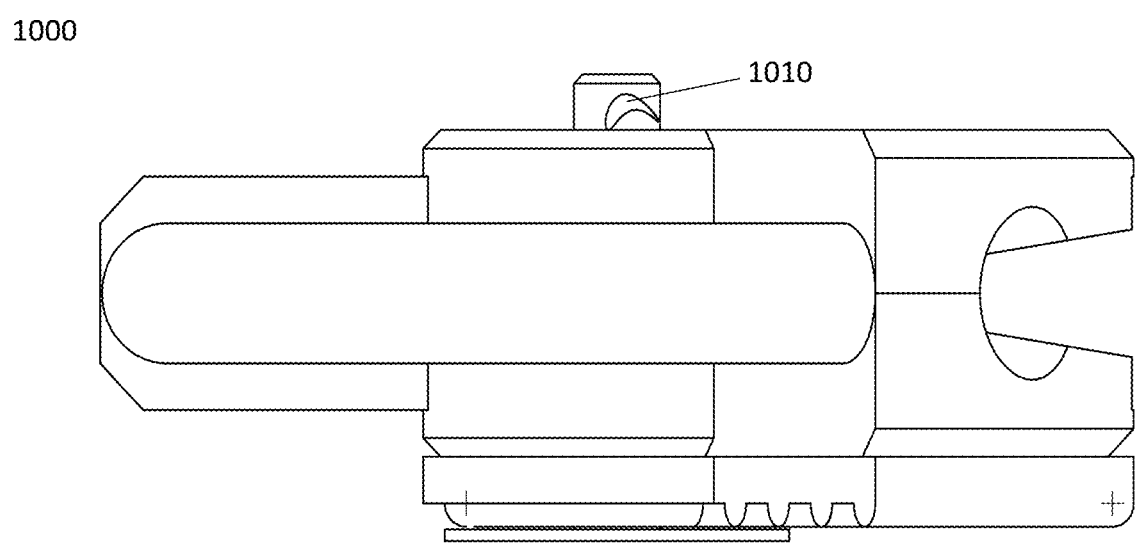
FIG. 10 shows a close-up cross-sectional view of an embodiment of a modular linkage comprising a tensioning anchor.
Figure 22:
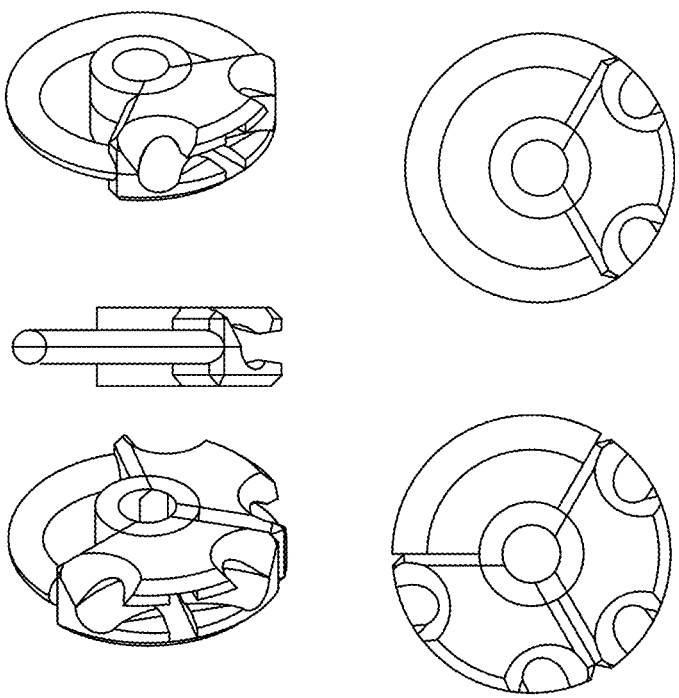
FIG. 22 shows isometric, top, and cross-sectional views of an embodiment of modular linkages with no beams.

The modular linkages are a novel structure that can be configured in a number of ways to create an adjustable custom socket for the user. An embodiment of the prosthesis system comprises of minor modular linkages 810 and major modular linkages 910. In this embodiment, illustrated in FIGS. 8 and 11, minor modular linkages comprise of a central tube 1110, a minor solid sector 1120 extending from and wrapping around approximately one-third of an exterior side of the central tube, a beam 1130 extending from the diametrically opposite exterior side of the central tube, and a curved member 1140 arcing from one radius line of the minor solid sector's end, through the beam's lateral end, to the other radius line of the minor solid sector's end. As illustrated in FIGS. 9 and 12, major modular linkages may comprise of a central tube 1210, a major solid sector 1220 extending from and wrapping around approximately two-thirds of an exterior side of the central tube, a beam 1230 extending from the diametrically opposite side of the central tube, and a curved member 1240 arcing from one radius line of the major solid sector's end, through the beam's lateral end, to the other radius line of the major solid sector's end. FIGS. 6 and 7 show a cross-sectional top view of a major 600 and minor 700 modular linkage. In this embodiment, the modular linkages are symmetric about the "A" axis 610/710. FIG. 22 illustrates other embodiments of modular linkages which may vary the number of beams 2200 and curved members to allow for variation in the number of interconnecting linkages. Furthermore, embodiments of modular linkages are not limited to symmetrical or circular shapes. For example, a modular linkage may comprise of a straight member instead of a curved member to achieve a triangular configuration. A user can then select the modular linkage most appropriate to achieve their desired socket configuration.

Figure 15:
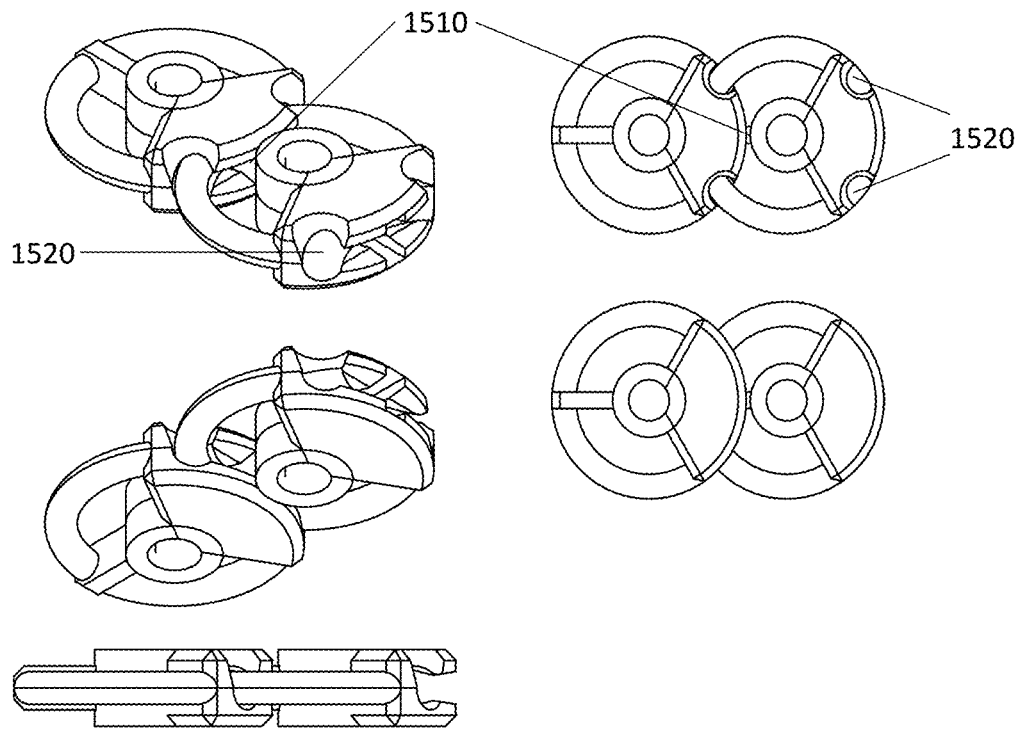
FIG. 15 shows embodiments of two modular linkages linked together with the beam and curved member of a modular linkage inserted into the hollow linking channel of another modular linkage.
Figure 16:
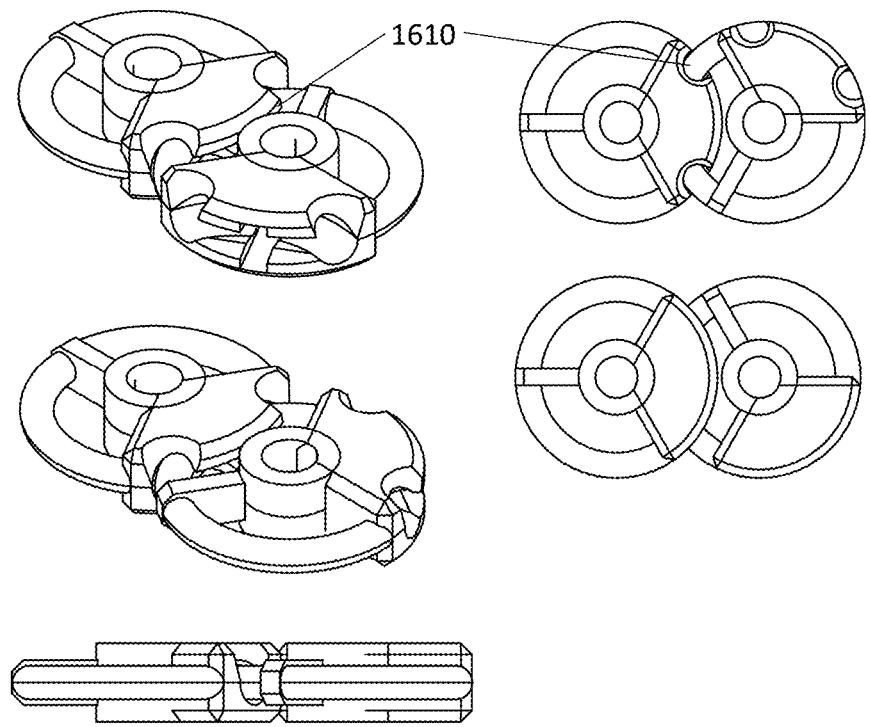
FIG. 16 shows isometric and cross-sectional views of embodiments of two modular linkages linked together with the only the curved member of a modular linkage inserted into the hollow linking channel of another modular linkage.
Figure 20:
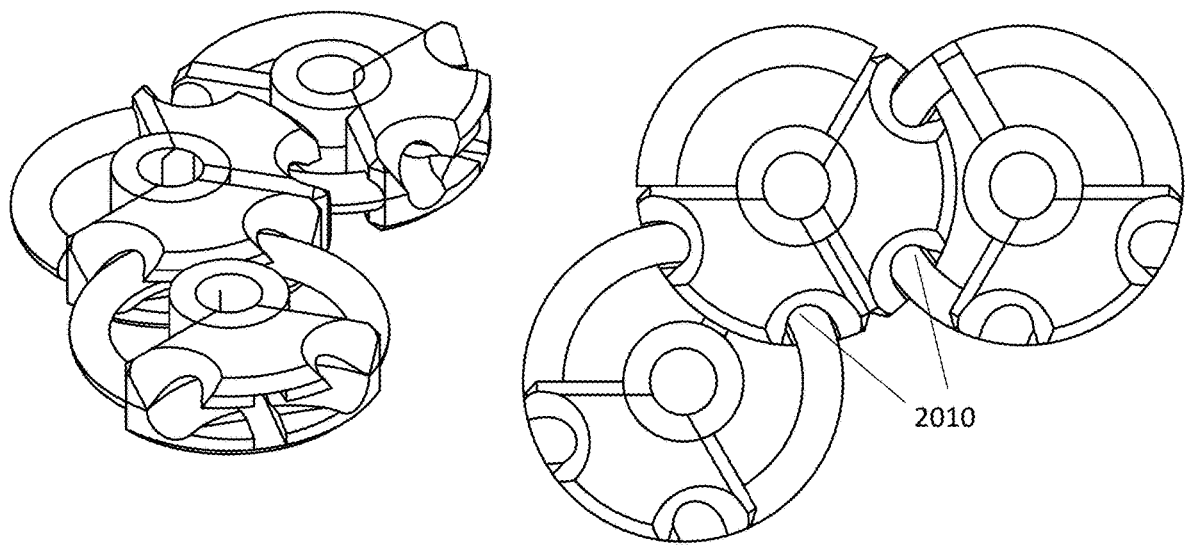
FIG. 20 shows an embodiment of a major modular linkage linked with two other modular linkages, with the beam and curved member of one modular linkage inserted into one hollow linking channel and only the curved member of a second modular linkage inserted into its other hollow linking channel.

An embodiment of the minor modular linkage consists of a hollow linking channel 1150 that runs along the minor solid sector. As illustrated in FIGS. 15, 16, and 20, the hollow linking channel may be configured so that another modular linkage may be connected by inserting either the curved member of another modular linkage alone 1610 or the curved member and beam of the other modular linkage 1510. An embodiment of the major modular linkage may consist of two hollow linking channels 1250 that run along the major solid sector. This allows two modular linkages to insert into a major modular linkage 2010. Other embodiments of the modular linkages may incorporate a different number of hollow linkage channels allowing for variation in the number of interconnecting linkages. Furthermore, the hollow linking channels may contain a directionally biased snapping mechanism to link modular linkages once they are inserted. The direction and axis of insertion 1510/1610 may be orthogonal to the direction and axis of linkage 2110. This permits a maximum load that is greater than the force required to link the modular linkages because the direction of insertion is different than the direction of linkage. For example, the maximum load is higher in an embodiment where modular linkages insert horizontally but link vertically. A more detailed discussion on the range of motion of a modular linkage is described below.

The disclosed adjustable prosthesis system provides a cost-effective and easy-to-use means of adjusting the size and shape of the socket to correspond with changes in the user's limb. The modular linkages may be assembled in any number of configurations to fit the user's limb negating the need for the socket to be remolded, remanufactured, realigned, and refit if a user's limb changes in size. Instead, individual modular linkages easily integrate and separate allowing for seamless changes in the socket's length, scale, or shape to accommodate changes to the user's limb. Users do not need to see a prosthetist every time an adjustment is needed, and prosthetists do not have to undergo a labor-intensive adjustment process in the event they do.

In addition, modular linkages are designed to be cost effective. Modular linkages are discrete repeating units that make up the disclosed prosthesis system. In some embodiments a modular linkage can be constructed of one or more of acrylonitrile butadiene styrene, poly ether ketone, polyetherketoneketone, polyetherimide, acrylonitrile styrene acrylate, polyethylene terephthalate, polycarbonate, polylactic acid, and other material known or used by those skilled in the art. An embodiment of a modular linkage may be constructed from an injection mold allowing for mass-production. An embodiment of a modular linkage measures 23 mm in diameter but embodiments may range in size from 5 mm to 40 mm in diameter. Consequently, modular linkages may have a low cost per unit because they require little material to make. Moreover, each individual modular linkage is asymmetric in design, giving rise to anisotropic global behaviors for the assembled socket, allowing it to serve multiple different functions. For example, a modular linkage also controls the rigidity and range of motion of the socket. This is described in more detail below. In sum, the modular linkages can be mass-produced to be sold at very low cost and assembled with little to no expert assistance.

Figure 3:
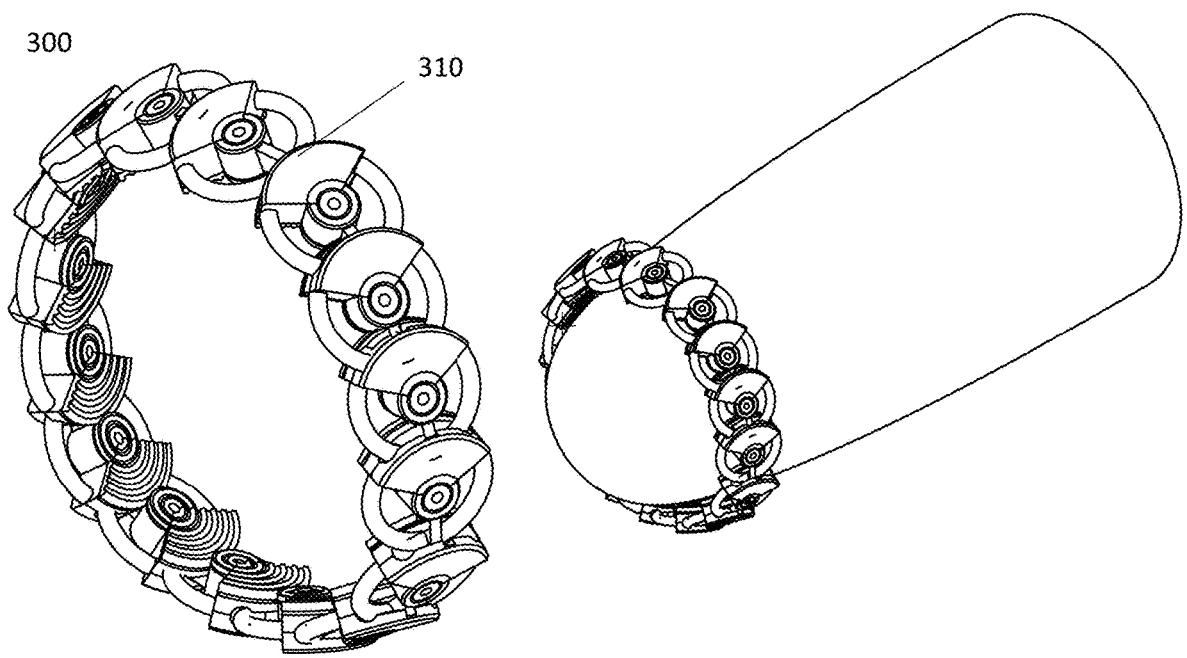
FIG. 3 is an embodiment of the mechanical coupling element comprising of repeating and interconnecting major and minor modular units placed on a user's residual limb.
Figure 17:
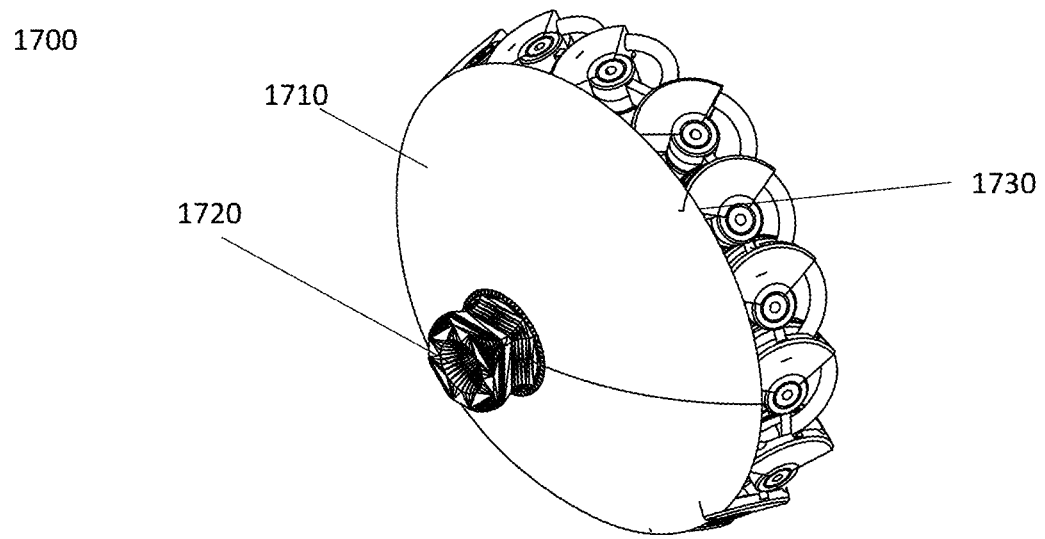
FIG. 17 shows an embodiment of a solid mechanical coupling element that may connect to a prosthesis on one side and a plurality of modular linkages on the other.
Figure 18:
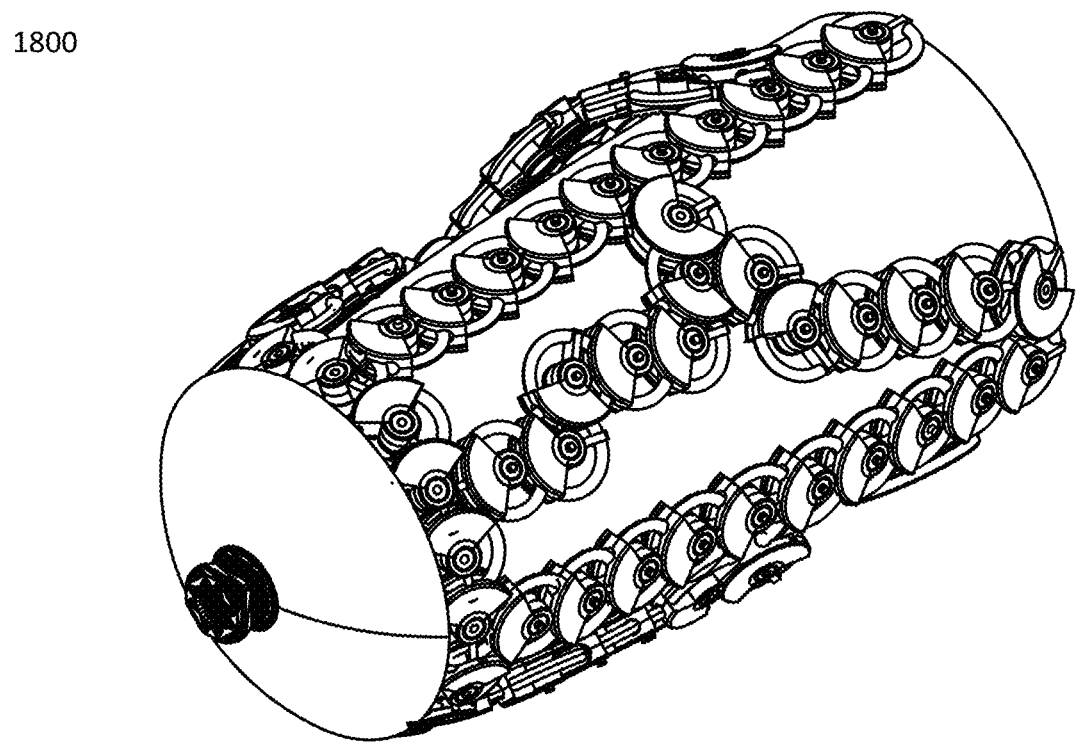
FIG. 18 is an embodiment of the disclosed prosthesis system in which the socket connects to a solid mechanical coupling element.

An embodiment of the mechanical coupling element comprises of interconnecting modular linkages 310 as illustrated in FIG. 3. In other embodiments, like the one illustrated in FIGS. 17 and 18, the mechanical coupling element may comprise of a solid element 1710. One side of the mechanical coupling element will connect to the network of modular linkages 410/1730 that comprise the socket using the same linking mechanism as individual modular linkages. For example, a curved member alone or a curved member and beam from the mechanical coupling element can be inserted into the hollow linking channels of a plurality of modular linkages that comprise the socket 410. The other side of the mechanical coupling element will connect to the prosthesis using coupling mechanisms known to persons of ordinary skill in the art 1720.

Elements Controlling the Prosthesis System's Fit

Figure 5:
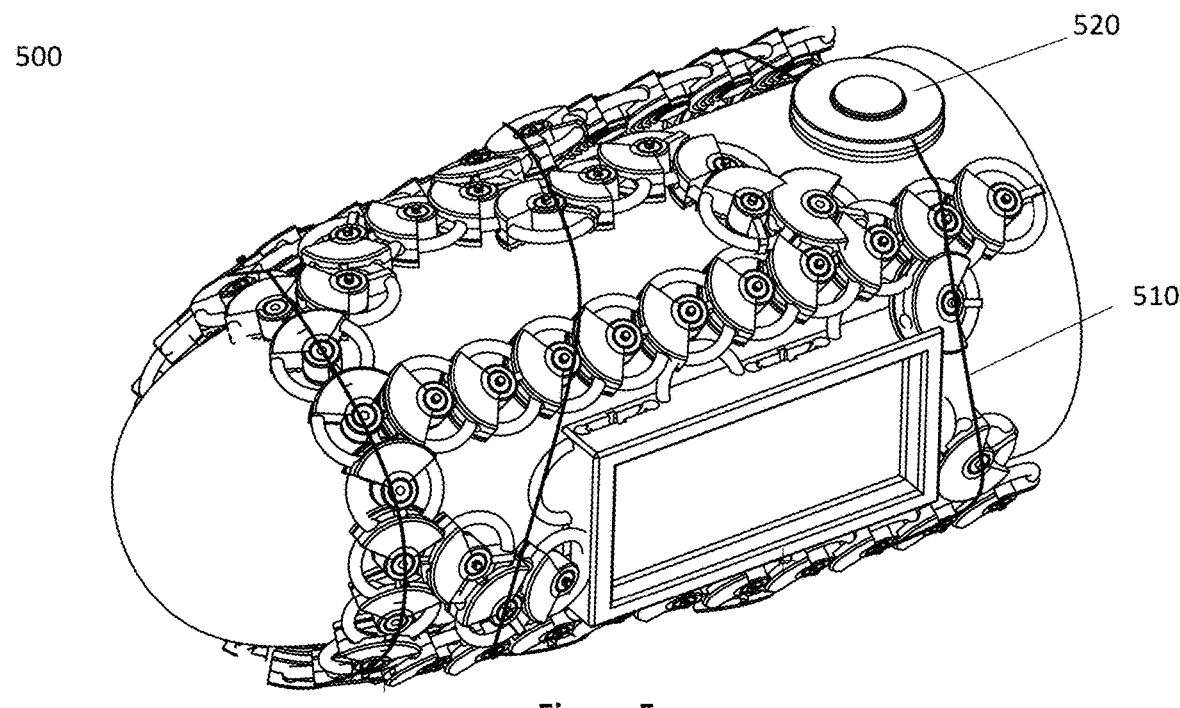
FIG. 5 is an embodiment of the prosthesis system further comprising one or more tensioning elements that form a lacing system which runs through tensioning anchors on the modular linkages and the tensioner.

In some embodiments, such as the one illustrated in FIG. 5, the prosthesis system comprises of tensioning elements 510 to secure the modular linkages to the user's limb. The tensioning elements together may comprise a lacing system that wraps around the socket. FIG. 5 illustrates an embodiment of a modular linkage that further comprises of tensioning anchors 1010 which pass through from the medial side of the modular linkage to the side distal to the user's limb. Tensioning anchors permit guidance of a tensioning element through a center of the tensioning anchor so as to create an adjustable suspension. In turn, this permits the tension element to slide as its length changes, resulting in greater or lesser hoop stress and circumferential pressure on the user's limb. As illustrated in FIG. 5, the tensioning elements are attached to a tensioner 520 which is configured to allow the user to adjust the tension. In an embodiment, the tensioner may be configured as a ratcheting dial. The tensioning system offers multiple advantages in that it allows the user to adjust the socket's fit without clinical assistance. Moreover, a user requires only one hand to adjust the tension which negates or reduces the need for another individual's assistance. In some embodiments, the tensioning elements can be constructed of one or more of stainless-steel tensioning cable, other metal wire, string, nylon, or flexible plastic.

Figure 11:
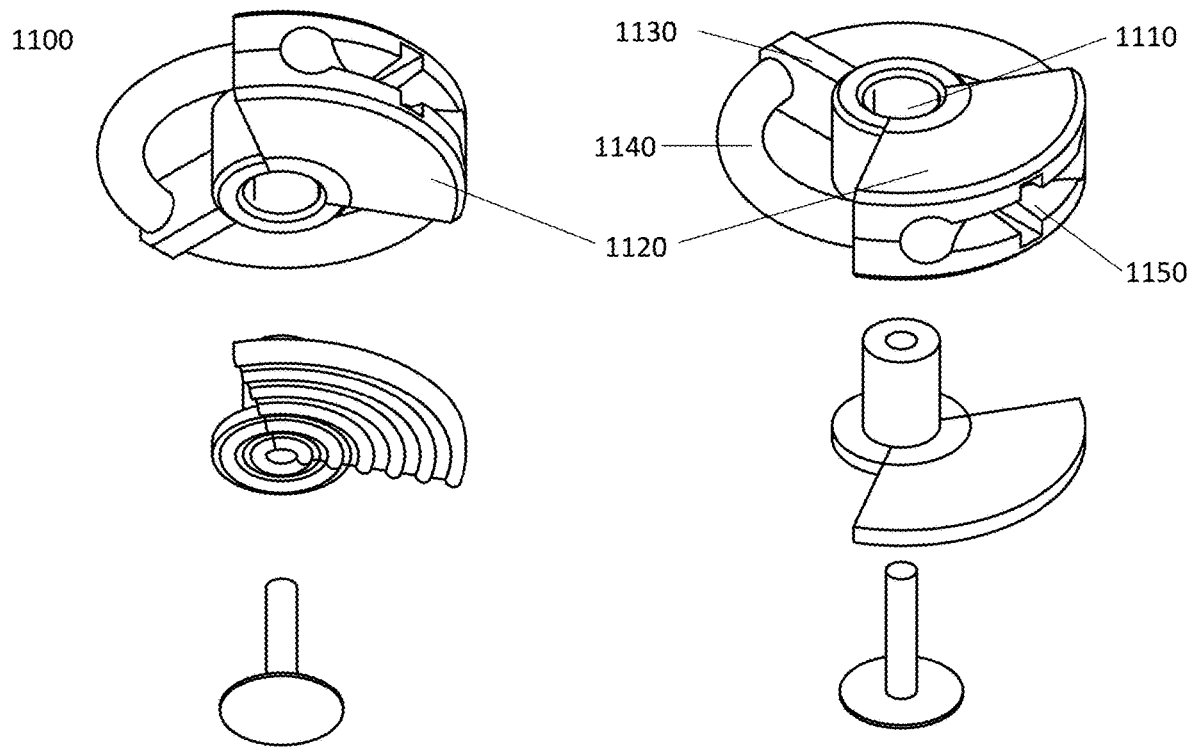
FIG. 11 shows an exploded view of embodiments of individual components of a minor modular linkage including a frictional element and sensor.
Figure 12:
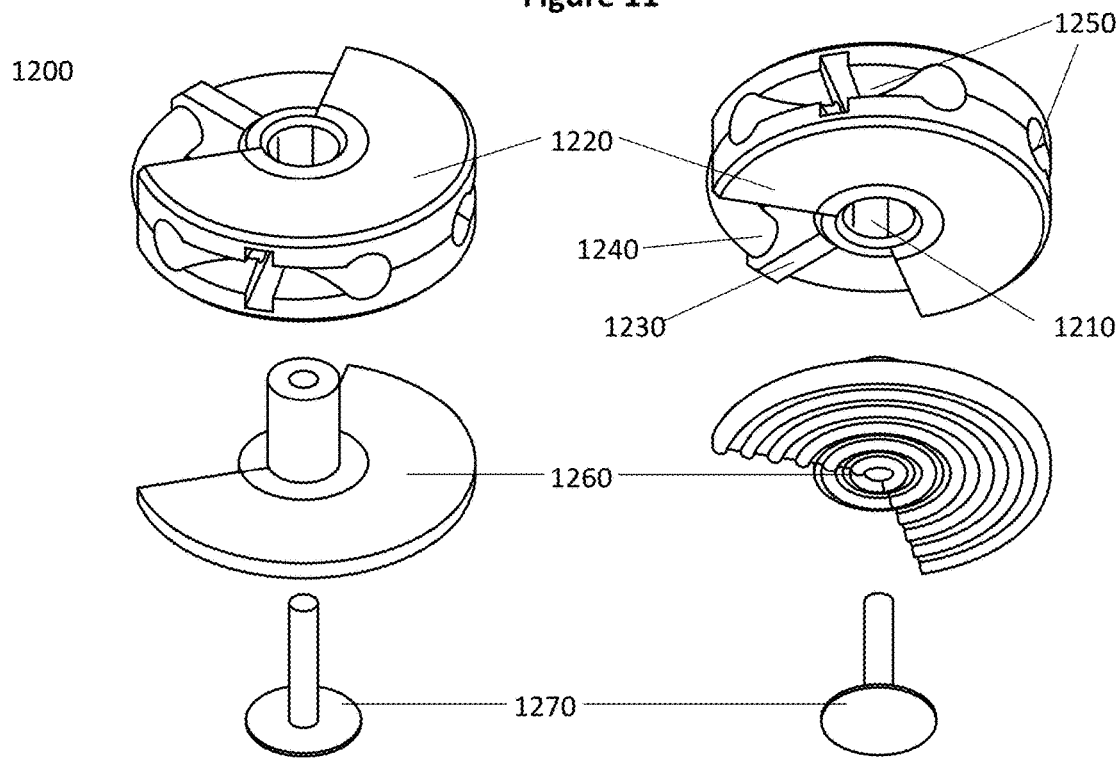
FIG. 12 shows an exploded view of embodiments of individual components of a major modular linkage including a frictional element and sensor.
Figure 13:
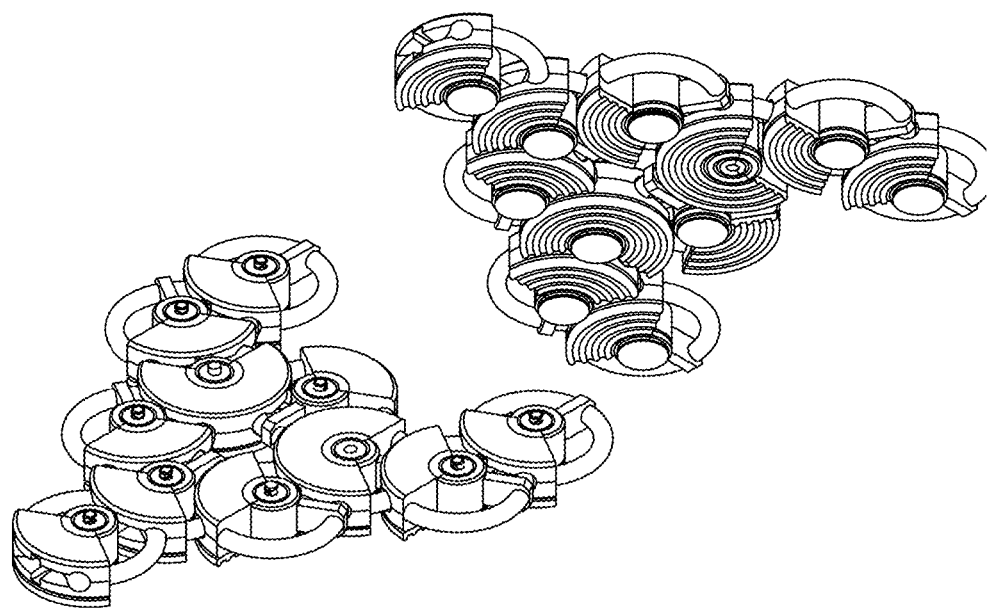
FIG. 13 shows isometric views of an embodiment of a network of repeating and interconnecting modular linkages.
Figure 14:
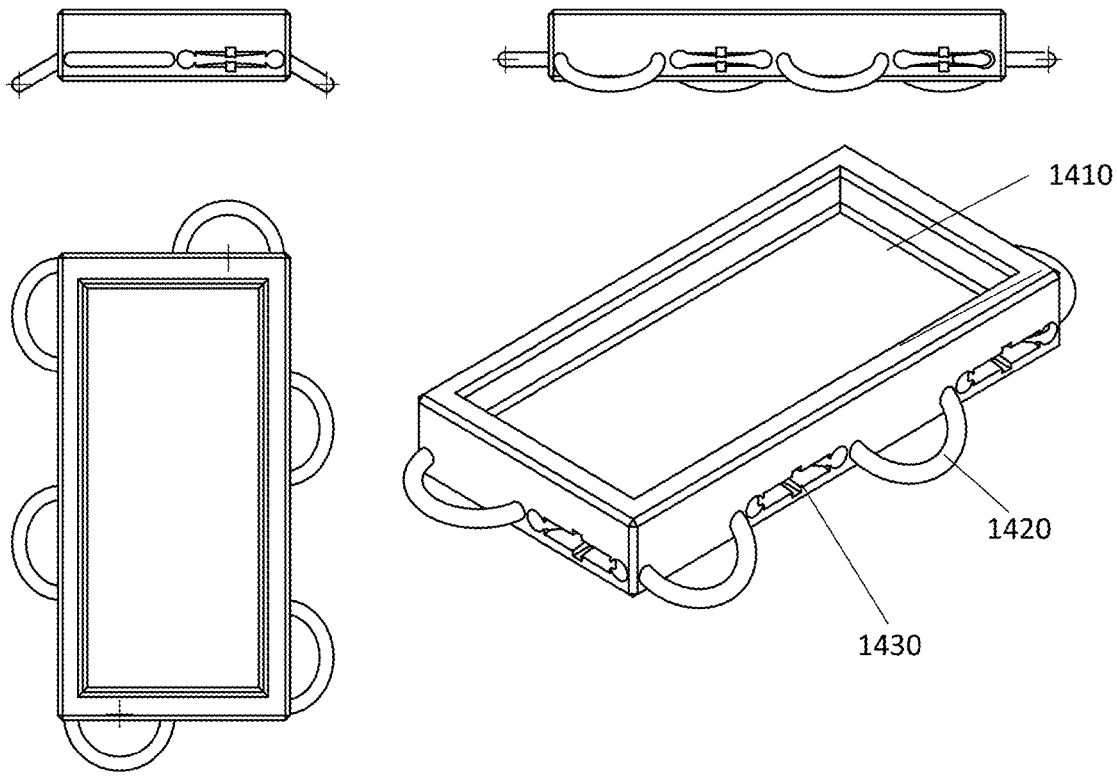
FIG. 14 shows top and bottom views of an embodiment of a functional modular device with curved members and hollow linking channels.

FIGS. 11 and 12 illustrate embodiments where a friction element 1160/1260 partially overlaps the central tube and fully overlaps the minor or major solid sector of the modular linkage. In another embodiment, the central tube is configured to allow the connection of a replaceable friction element medial to the user's limb via an insertable member that fits into the central tube. The friction element may comprise of one or more of silicon, polyurethane, rubber, or any material known or used by those having skill in the art. The friction element may be configured to distribute load and reduce how tight the socket must be configured to a user's limb. The friction element provides friction between the modular linkage and the layer below the friction element. In some embodiments this layer may be the user's skin. In others the prosthesis system comprises of a sleeve or conformal undercoating between the user's limb and modular linkage to reduce contact pressure. Therefore, the material should be soft and have a high coefficient of friction. The undercoating may be constructed of one or more of foam, rubber, silicone, polyurethane, and other materials that reduce contact pressure. The friction element and undercoating allow the socket to remain in place around the user's limb and provide a form of padding to reduce pressure from the socket on the user's skin.

Figure 19:
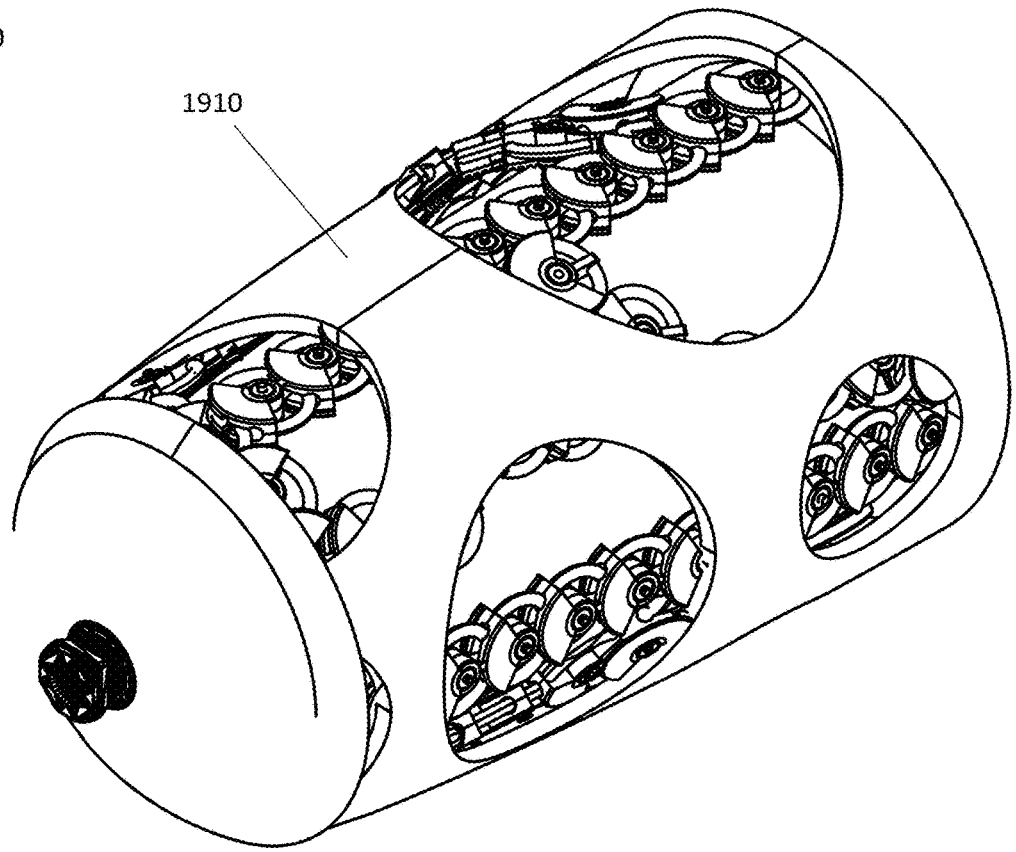
FIG. 19 shows an embodiment of the outer load-sharing structure around a socket comprising modular linkages.

FIG. 19 illustrates an embodiment of the disclosed system further comprise an outer load-sharing structure 1910 that redistributes load across the socket to increase the load-bearing capacity of the prosthesis system. This would make the socket more rigid and prevent the prosthesis from buckling. In an embodiment, the outer load-sharing structure may also be configured to secure the socket to the limb so that a tensioning element isn't needed. Furthermore, in some embodiments the outer load-sharing structure may also function as a covering over the prosthesis which a user can customize and replace.

Current prosthesis systems must be carefully molded by a prosthetist to comfortably fit a user's limb and require the use of padding liners for comfort. The disclosed system offers more versatile and granular means of achieving such comfort. The prosthesis system can be used with friction elements alone or with a sleeve. In addition, the user can use the tensioning system to adjust tension across the socket. The tensioning system allows the socket to adapt to volumetric fluctuations in the size of a limb without the need to add or remove padding liners. Finally, the outer load-bearing structure can also reduce contact pressure.

Elements Controlling the Prosthetic System's Range of Motion

Figure 21:
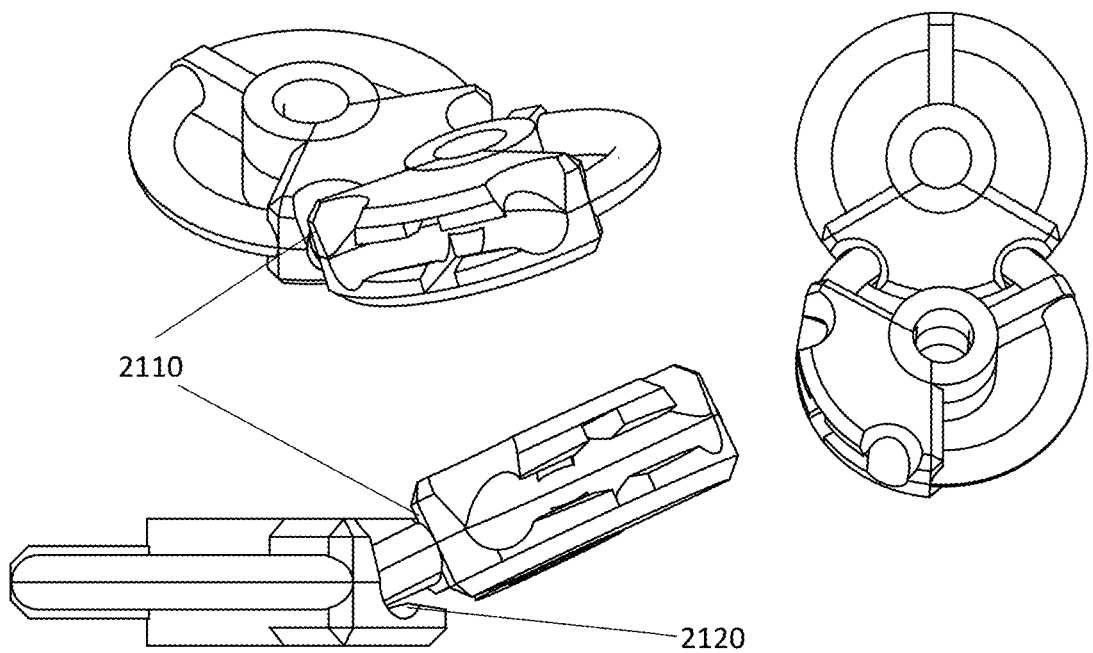
FIG. 21 shows isometric, top, and cross-sectional views of an embodiment of the modular linkage's range of motion and the asymmetric nature of a notch.

The configurable and asymmetric nature of modular linkages allows a user or prosthetist to control the range of motion of the prosthesis system. The linkage of several modular linkages, when assembled in a specific and engineered configuration, results in the formation of a metamaterial, whereby the material as a whole behaves very differently than each component would behave on its own. The insertion of a first modular linkage into a second modular linkage via the directionally biased snapping mechanism with both the curved member and beam, restricts the range of motion of the interconnecting modular linkages to zero degrees of freedom. If the modular linkages are linked using only a curved member, the interconnecting modular linkages retain one degree of freedom, the yaw. In a three-dimensional plane this refers to movement about the Y-axis. Therefore, the number of beams in a modular linkage may control the range of motion within a configured socket. Some embodiments of the modular linkages further comprise of notches 1520 located at diametrically opposite ends of the hollow linking channels, as illustrated in FIG. 15. These notches allow for additional range of motion. When a modular linkage with notches is linked via a curved member alone, the interconnected modules have a second degree of freedom, the pitch, 2110 as illustrated in FIG. 21. On a three-dimensional plane this refers to movement about the X-axis. However, the asymmetric nature 2120 of the notches limits these modular linkages to either pitch-up or pitch-down motion. Embodiments of notches may vary in size and position to allow for varying ranges of motion. Collectively, these features allow the user or prosthetist to configure the prosthesis system based on the needs of the user. For example, some users might prefer additional range of motion in the socket, while others prefer a more rigid structure. If the user's preference changes, they can easily reconfigure the prosthesis system. This control over range of motion permits formation of different global mechanical properties for the socket, either in part or in whole. Some configurations of modular linkages would give rise to tight radii of curvature and low stiffness, while other configurations would give rise to straight and stiff sections. The disclosed invention allows for a wide range of socket mechanical properties, variable within user-defined regions of a single socket, to be composed from a single material with very low unique part count.

Functional Elements

Figure 4:
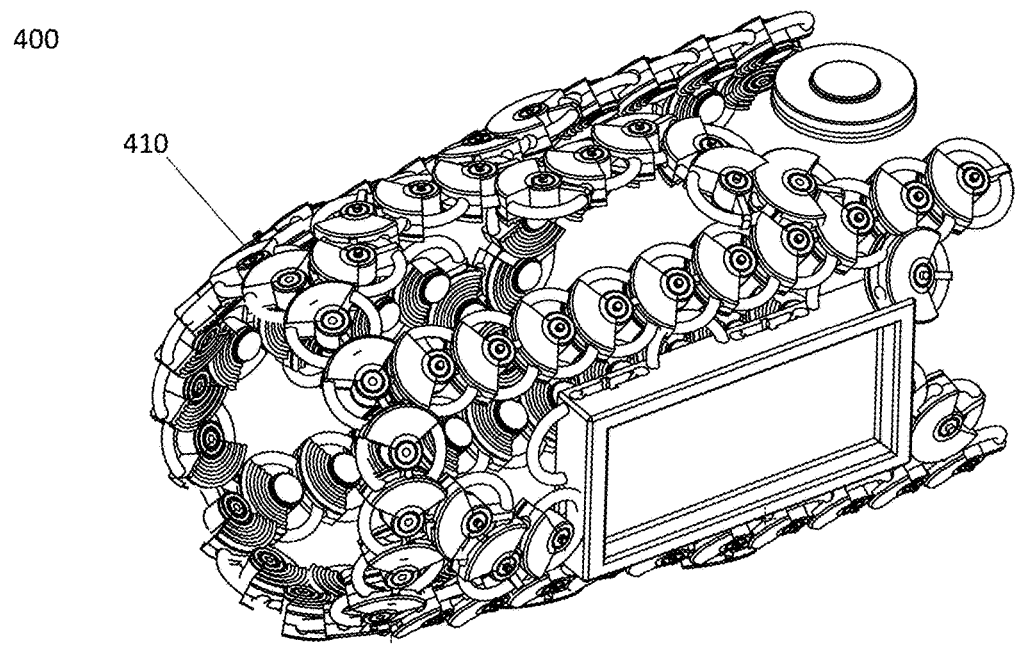
FIG. 4 is an embodiment of the prosthesis system further comprising a functional module dock and a tensioner and where the mechanical coupling element connects to a network of modular linkages that comprise a socket.

The prosthesis system may be configured to connect to a functional element 2320. Functional elements may include one or more of GPS tracking device, interactive display, personal cellular phone, motor, batteries, data storage and communication device, graphical user interface, buttons, microphone, speaker, processing unit, and other elements known or used by a person skilled in the art. In some embodiments the prosthesis system attaches to a functional element through a functional module dock, 1410 as illustrated in FIG. 4. In others, the functional element may attach without the use of a dock. An embodiment of the functional module dock comprises of repeating curved members 1420 and hollow linking channels 1430 along the exterior edge of the dock. This allows the functional module to connect to modular linkages using the same directional snapping mechanism described above. Integration of functional elements with the prosthesis system provides users with more functionality and cam allow clinicians to monitor patients more closely.

Figure 23:
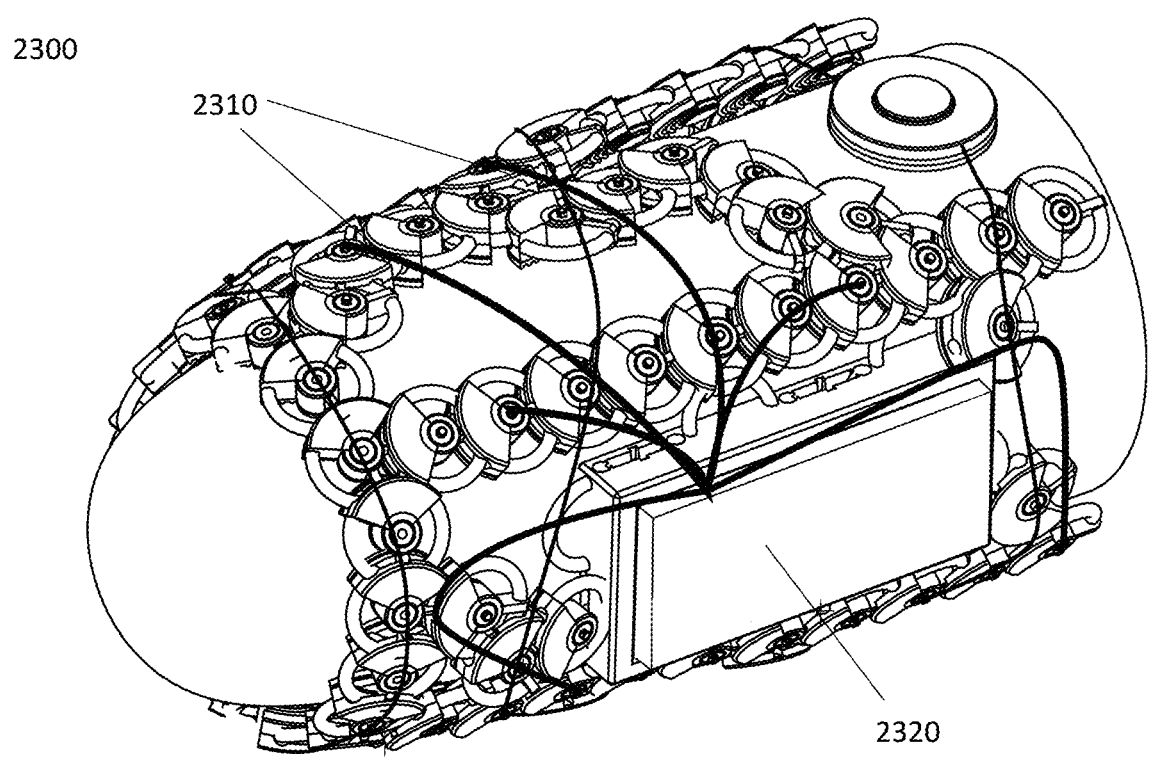
FIG. 23 shows an embodiment of the disclosed prosthesis system further comprising a sensor system and processing unit.

Embodiments of the modular linkages further comprise a central tube that is configured to contain a sensor 1170/1270 medial to the user's limb. FIG. 23 illustrates an embodiment of the disclosed prosthesis system configured with a sensor system. The plurality of wires 2310 of the sensor system run through the central tube and out the distal side of the central tube. The sensor system communicates with a processing unit 2320 to collect user data. For example, data may include the user's heart rate, temperature, blood pressure, and the prosthesis angle and moment. The disclosed sensor system improves on currently available systems because it may be mass-produced at low cost, requires little customization, and significantly reduces the effort and skill prosthetists require to implement such system. Furthermore, the modular and repeating nature of the socket assembly provides a system by which sensors and stimulating elements can be selectively and precisely located and relocated along the user's limb without the need to embed these elements in the socket during manufacture. This permits the disclosed prosthesis system to be modified over time without the need to manufacture a new socket. In some embodiments the processing unit is a system for data storage. In others the processing unit allows for data analysis and communicates results to a user's clinical provider or the user themself. Furthermore, an embodiment of the sensor system incorporates artificial intelligence to analyzes and learn from data collected by the sensor system.

In some embodiments the central tube further comprises a stimulating element that is controlled by a processing unit on the basis of input received at the sensor system. Individuals often have a hard time learning how to use a prosthetic limb because they are unable to experience sensations in the prosthesis. Some even experience phantom limb syndrome where they "feel" their missing limb in a perceived position different from the prosthesis. Consequently, a user requires a lot of time to learn how to operate a prosthesis. The stimulating element addresses these issues by stimulating a user's residual limb based on input from the sensor system. This allows for a more natural approach to sensory learning which enables users to engage with prostheses more closely and master use of them more efficiently. In addition, a clinical expert may utilize the stimulating element to assist with a patient's physical therapy.

A person skilled in the relevant art will recognize that other configurations and arrangements can be used without departing from the spirit and scope of the disclosed invention. It will be apparent to a person skilled in the relevant art that this invention can also be employed in a variety of other systems and applications.

What is claimed is:

1. An adjustable prosthesis system comprising:
 a plurality of major modular linkages interconnected with a plurality of minor modular linkages to form a socket around a limb of a user;
 at least one tensioning element securing the socket to the limb;
 at least one tensioner attached to the at least one tensioning element, the at least one tensioner configured to allow for tension adjustment by the user;
 wherein each of the major modular linkages includes a central tube, a major solid sector extending from and wrapping around nominally two-thirds of an exterior side of the central tube, a beam extending from a diametrically opposite exterior side of the central tube, and a curved member extending circumferentially from a first end of the major solid sector, through a lateral end of the beam, to a second end of the major solid sector; and
 wherein each of the minor modular linkages includes a central tube, a minor solid sector extending from and wrapping around nominally one-third of an exterior side of the central tube, a beam extending from a diametrically opposite exterior side of the central tube, and a curved member extending circumferentially from a first end of the minor solid sector, through a lateral end of the beam, to a second end of the minor solid sector.

2. The adjustable prosthesis system of claim 1, comprising a mechanical coupling element to join the socket and a prosthesis, distal to a joint of the user, by attaching to at least one of the plurality of major modular linkages or the plurality of minor modular linkages.

3. The adjustable prosthesis system of claim 2, wherein the mechanical coupling element comprises a configuration of interconnecting modular linkages.

4. The adjustable prosthesis system of claim 1, wherein at least one modular linkage of the plurality of major modular linkages or at least one modular linkage of the plurality of minor modular linkages includes a tensioning anchor on a side distal to the limb that is configured to permit guidance of a tensioning element through a center of the tensioning anchor so as to create an adjustable suspension.

5. The adjustable prosthesis system of claim 1, wherein the plurality of major modular linkages and the plurality of minor modular linkages each comprise one or more of acrylonitrile butadiene styrene, polyether ether ketone, polyetherketoneketone, polyetherimide, acrylonitrile styrene acrylate, polyethylene terephthalate, polycarbonate, and polylactic acid.

6. The adjustable prosthesis system of claim 1, wherein at least one of the plurality of major modular linkages or the plurality of minor modular linkages is configured to permit a connection of a functional module dock which is configured to hold one or more functional elements, comprising one or more of a GPS tracking device, an interactive display, a personal cellular phone, a motor, batteries, a data storage and communication device, a graphical user interface, buttons, a microphone, a speaker, and a processing unit.

7. The adjustable prosthesis system of claim 1,
wherein the minor solid sector has a hollow linking channel running along the minor solid sector and configured so that another modular linkage from either the plurality of major modular linkages or the plurality of minor modular linkages may be connected by inserting either the curved member of the other modular linkage alone or the curved member and the beam of the other modular linkage therein; and
wherein the major solid sector has two hollow linking channels along either side of the major solid sector and configured so that other modular linkages from at least one of the plurality of major modular linkages or the plurality of minor modular linkages may be connected into one or both hollow linking channels by inserting either the curved member of the other modular linkages alone or the curved member and the beam of the other modular linkages therein.

8. The adjustable prosthesis system of claim 7,
wherein the hollow linking channels of the major solid sectors and the hollow linking channels of the minor solid sectors each contain a directionally biased snapping mechanism configured to allow insertion of the other modular linkages therein.

9. The adjustable prosthesis system of claim 8, wherein a direction and axis of insertion is orthogonal to a direction and axis of linkage.

10. The adjustable prosthesis system of claim 8, wherein a range of motion of the adjustable prosthesis system can be configured by a connection of modular linkages;
wherein insertion of both the curved member and the beam of a first modular linkage into the hollow linking channel of a second modular linkage limits range of motion; and
wherein insertion of only the curved member of the first modular linkage into the hollow linking channel of the second modular linkage enables range of motion.

11. The adjustable prosthesis system of claim 8, wherein each major modular linkage of the plurality of major modular linkages and each minor modular linkage of the plurality of minor modular linkages comprises diametrically opposite notches on either side of the hollow linking channel allowing for further range of motion orthogonal to an axis of linkage.

12. The adjustable prosthesis system of claim 1, wherein a friction element partially overlaps the central tube and fully overlaps the minor solid sector or the major solid sector of at least one modular linkage of the plurality of minor modular linkages or the plurality of major modular linkages;
wherein the friction element is configured to distribute load and reduce how tight the socket must be configured to remain on the limb.

13. The adjustable prosthesis system of claim 12, wherein the central tube is configured to allow connection of a replaceable friction element medial to the limb via an insertable member that fits into the central tube.

14. The adjustable prosthesis system of claim 1, wherein the central tube is configured to contain a sensor system medial to the limb, with a plurality of wires of the sensor system running through the central tube and out of a distal side of the central tube;
wherein the sensor system is in communication with a processing unit.

15. The adjustable prosthesis system of claim 14, wherein the central tube is configured to contain a stimulating element that is controlled by the processing unit based on an input received at the sensor system.

16. The adjustable prosthesis system of claim 1, wherein the at least one tensioning element includes a lacing system.

17. The adjustable prosthesis system of claim 1, wherein the tensioner includes a ratcheting dial tensioner which the user can operate using one hand.

18. The adjustable prosthesis system of claim 1, comprising an outer load-sharing structure that redistributes load to improve load spread and transfer around the limb.

* * * * *